United States Patent
Ruminson

[11] Patent Number: 6,156,011
[45] Date of Patent: Dec. 5, 2000

[54] SYRINGE NEEDLE GUARD

[76] Inventor: Wallace E. Ruminson, 444 W. Putnam, Porterville, Calif. 93257

[21] Appl. No.: 09/407,242

[22] Filed: Sep. 28, 1999

Related U.S. Application Data

[60] Provisional application No. 60/135,598, May 24, 1999.

[51] Int. Cl.⁷ .................................................. A61M 5/00
[52] U.S. Cl. ........................................... 604/192; 604/263
[58] Field of Search ..................................... 604/192, 198, 604/263, 110, 187

[56] References Cited

U.S. PATENT DOCUMENTS

| | | |
|---|---|---|
| D. 302,296 | 7/1989 | Harmony . |
| 4,631,057 | 12/1986 | Mitchell . |
| 4,654,034 | 3/1987 | Masters et al. . |
| 4,737,144 | 4/1988 | Choksi . |
| 4,740,204 | 4/1988 | Masters et al. . |
| 4,799,927 | 1/1989 | Davis et al. . |
| 4,838,871 | 6/1989 | Luther ...................... 604/192 |
| 4,883,470 | 11/1989 | Haindl . |
| 4,986,817 | 1/1991 | Code . |
| 4,998,924 | 3/1991 | Ranford ............... 604/192 X |
| 5,002,536 | 3/1991 | Thompson et al. . |
| 5,021,049 | 6/1991 | Howard . |
| 5,026,345 | 6/1991 | Teringo . |
| 5,057,088 | 10/1991 | Narayanan et al. ............. 604/198 |
| 5,066,279 | 11/1991 | Russell . |
| 5,098,403 | 3/1992 | Sampson ................ 604/263 X |
| 5,190,532 | 3/1993 | Yu . |

*Primary Examiner*—John D. Yasko
*Attorney, Agent, or Firm*—Kelly Bauersfeld Lowry & Kelley, LLP

[57] ABSTRACT

An improved needle guard is provided for quick and easy mounting onto a syringe to protect against accidental or inadvertent contact with a hypodermic needle. The needle guard comprises a generally cylindrical sleeve of relatively lightweight yet relatively stiff plastic material formed in a tubular configuration and longitudinally split to define adjacent marginal edges which may overlap. These longitudinal marginal edges are adapted for sufficient separation at a front or distal end of the guard sleeve to permit sliding press-fit placement of the guard sleeve onto the syringe barrel, in a position surrounding a hypodermic needle protruding from the syringe barrel. A lock member such as a thumbscrew is mounted on the guard sleeve adjacent the rear or proximal end thereof, and can be manipulated to engage and lock with the syringe barrel in a position with a forward or distal end of the guard sleeve surrounding and protecting the hypodermic needle against inadvertent or accidental contact.

20 Claims, 3 Drawing Sheets

SYRINGE NEEDLE GUARD

This application claims benefit to provisional application No. 60/135,598 filed May 24, 1999.

BACKGROUND OF THE INVENTION

This invention relates generally to needle stick prevention devices for use with medical syringes, to protect against accidental or inadvertent contact with a hypodermic needle. More particularly, this invention relates to an improved and relatively simple needle guard adapted for safe and easy mounting onto a syringe, and further wherein the improved needle guard may be used with a variety of different syringes having different barrel sizes.

Syringes are used widely throughout the medical profession for administering medication to a patient, and also for drawing body fluid from a patient. A typical medical syringe comprises a hollow syringe barrel in combination with a plunger received slidably therein for delivering or drawing fluid respectively from or into the barrel interior via a hypodermic needle protruding from a front or nose end of the barrel. In recent years, in an effort to prevent the spread of infectious disease, medical syringes have commonly been produced in a lightweight and relatively inexpensive form suitable for disposal following a single use. However, syringe disposal inherently requires some handling of a used syringe by medical personnel, such that occasional accidental or inadvertent needle sticks can occur.

A variety of needle stick prevention devices have been proposed in an attempt to reduce or eliminate the occurrence of accidental or inadvertent needle sticks in the course of post-use syringe handling and disposal. In a typical form, a tube-shaped apparatus is mounted on the syringe barrel and adapted for manipulation between a retracted position exposing the hypodermic needle for use, and an advanced position intended to cover the hypodermic needle and thereby prevent accidental contact therewith. While such devices are capable of reducing incidents of inadvertent needle sticks, they have generally been relatively complicated in construction and thus typically add significantly to the overall cost of the medical syringe. Moreover, such devices have generally been limited to use with a syringe of a single barrel size, and have not been suited for use with syringes of a range of different barrel sizes.

The present invention relates to an improved syringe needle guard which overcomes these problems and disadvantages by providing a relatively simple and easy to use device which can be installed quickly and easily and safely onto a syringe barrel having a range of different barrel sizes to cover the hypodermic needle and thereby protect against accidental needle contact.

SUMMARY OF THE INVENTION

In accordance with the invention, an improved and relatively simple needle guard is provided for mounting onto a syringe to protect against accidental or inadvertent contact with a hypodermic needle. The needle guard comprises a generally cylindrical and longitudinally split sleeve for sliding and press-fit placement onto a syringe barrel to protrude forwardly therefrom in surrounding and protective relation to a hypodermic needle. A lock member on the guard sleeve is releasibly engageable with the syringe barrel to lock the sleeve in place.

In one preferred form, the guard sleeve is constructed from relatively lightweight yet relatively stiff plastic sheet material rolled and set in a normal tubular and partially collapsed configuration with closely adjacent longitudinal marginal edges which may be at least slightly overlapping or scrolled. In this normal configuration, the guard sleeve has a relatively small diametric size, preferably at least slightly less than the diametric size of a syringe barrel onto which the sleeve is to be mounted. The guard sleeve is installed onto the syringe barrel by sufficiently separating or unscrolling the longitudinal marginal edges at a front or distal end of the guard sleeve to accommodate reception of the syringe barrel therebetween. The guard sleeve is then advanced onto the syringe barrel with a press-fit and sliding movement with the marginal edges separating sufficiently in the course of such movement to fit the guard sleeve coaxially onto the syringe barrel, and with the guard sleeve expanding diametrically in size to fit snugly onto the syringe barrel. The guard sleeve is then positionally adjusted on the syringe barrel so that the front end of the guard sleeve protrudes forwardly at least slightly beyond the sharp pointed tip of a hypodermic needle protruding from a front end thereof to safeguard against accidental needle contact.

The lock member such as a thumbscrew is mounted on the guard sleeve adjacent the rear or proximal end thereof, and can be manipulated to engage and lock with the syringe barrel for securely retaining the guard sleeve thereon in a position with the front end of the guard sleeve preventing contact with the tip of the hypodermic needle. One or more radially outwardly protruding tabs may be formed on the guard sleeve adjacent the front end thereof to facilitate fingertip manipulation for initial separation of the sleeve marginal edges preparatory to placement onto the syringe.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
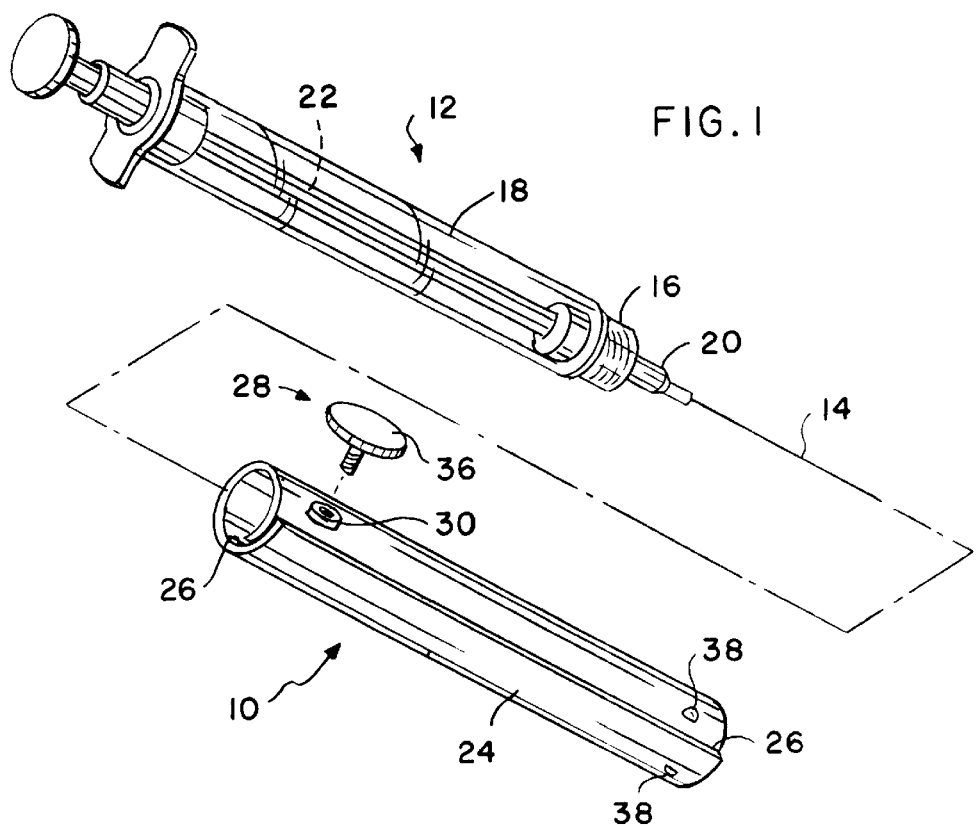
FIG. 1 is an exploded perspective view illustrating a syringe needle guard constructed in accordance with the invention for assembly with a syringe to protect against inadvertent contact with a hypodermic needle.

As shown in the exemplary drawings, an improved needle guard referred to generally in FIGS. 1–6 by the reference numeral 10 is provided for use with a medical syringe 12 having a pointed tip hypodermic needle 14 protruding from the front or nose end 16 of a syringe barrel 18. The needle guard 10 is designed for quick and easy mounting onto the syringe barrel 18 in a position surrounding and covering the needle 14, to prevent inadvertent or accidental contact with the needle 14. Accordingly, when the needle guard 10 is mounted on the syringe 12, accidental needle sticks are substantially prevented.

The improved needle guard 10 is designed for use with a conventional medical syringe 12 of the type having a hollow syringe barrel 18 with the hypodermic needle 14 supported at the barrel nose end 16 by means of a suitable fitting 20 or the like. A plunger 22 is received into an open rear end of the syringe barrel 18 for movement therein to dispense medication from the syringe, or alternately to draw fluid into the syringe. The geometric size of the syringe barrel 18 may vary in terms of barrel diameter and length, in accordance with the fluid volume capacity of the barrel. In one typical form, the syringe 12 is designed for disposal following a single use. The needle guard 10 is designed primarily for mounting onto the syringe barrel 18 subsequent to syringe use, to safeguard medical personnel and others against accidental contact with the used hypodermic needle 14. However, it will be recognized and understood that the improved needle guard 10 may additionally be used to protect against inadvertent needle contact prior to use of the syringe.

The needle guard 10 comprises a generally tubular and longitudinally split guard sleeve 24 constructed in the preferred form from a relatively lightweight yet structurally stiff sheet of plastic material which is rolled and set in a normal cylindrical and partially collapsed configuration with closely adjacent and preferably at least slightly overlapping or scrolled longitudinal marginal edges 26. In this normal configuration, the guard sleeve 24 has a relatively small diametric size (FIG. 1) which may be slightly less than the diametric size of the barrel 18 of the syringe 12 onto which the sleeve 24 is to be mounted. In addition, the guard sleeve 24 has a longitudinal length sufficiently greater than the length of the hypodermic needle 14, to permit a rear or proximal end of the sleeve 24 to be secured onto the barrel 18 such as at the barrel nose end 16, as will be described in more detail, with a front or distal end of the sleeve 24 protruding forwardly from the barrel nose end 16 to a position terminating at least slightly beyond the pointed tip of the needle 14.

Figure 2:
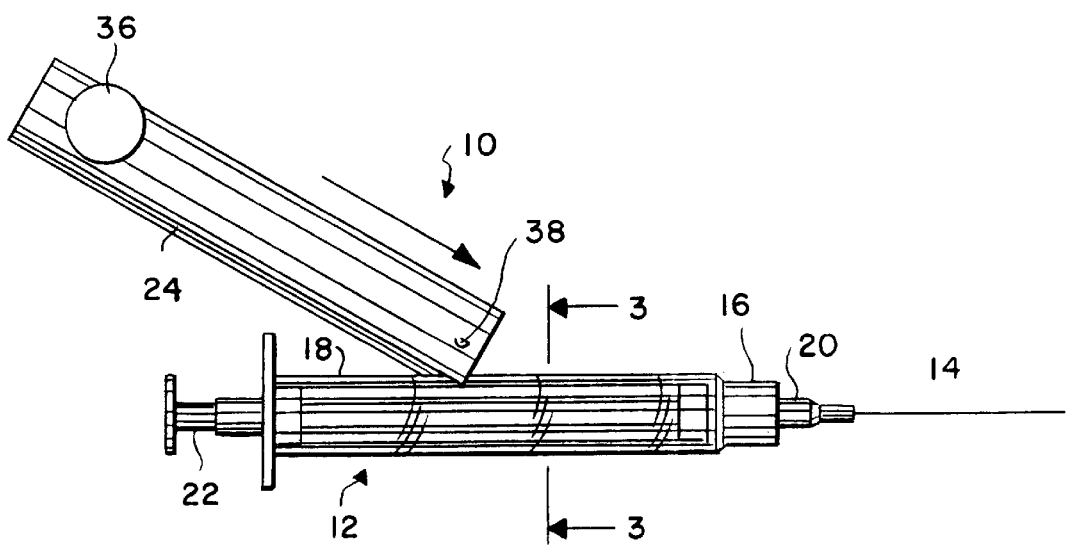
FIG. 2 is a side elevation view of the syringe depicted in FIG. 1, and illustrating initial deployment of the needle guard for mounting onto the syringe, with the needle guard shown in longitudinal section.
Figure 3:
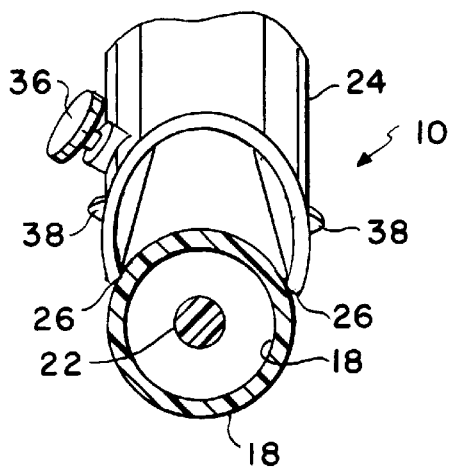
FIG. 3 is an enlarged transverse sectional view taken generally on the line 3—3 of FIG. 2.
Figure 4:
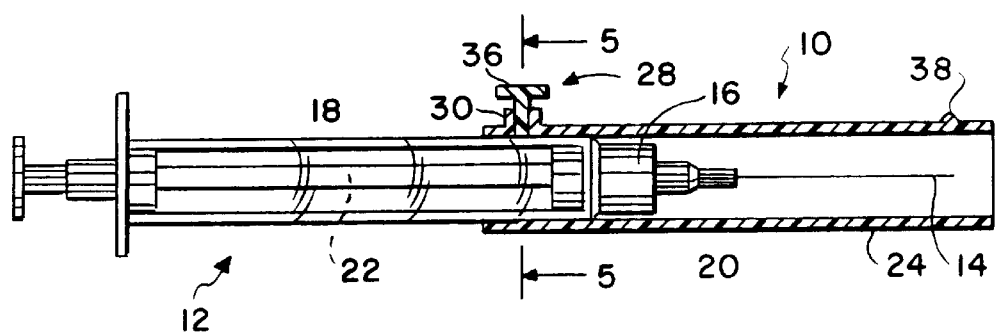
FIG. 4 is a side elevation view similar to FIG. 2, but showing the needle guard in a position fully installed and locked onto the syringe, with the needle guard again being shown in longitudinal section.

As shown in FIGS. 2 and 3, the guard sleeve 24 is installed onto the syringe barrel 18 by a combined sliding and press-fit motion. More particularly, the guard sleeve 24 has sufficient radial resilience to permit the longitudinal marginal edges 26 at the front or distal end of the guard sleeve 24 to be manually separated sufficiently to accommodate reception of the syringe barrel 18 therebetween. In this regard, small radially outwardly protruding tabs 38 are conveniently formed on the exterior of the guard sleeve 24 at or near the front end thereof for facilitated fingertip manipulation to separate these marginal edges 26. With the marginal edges 26 separated (FIG. 3), the front end of the guard sleeve 24 is then pressed onto the syringe barrel 18 with a forward sliding motion (illustrated by the arrow in FIG. 2), whereby the marginal edges 26 progressively separate from the front to the rear sleeve end as the guard sleeve 24 is fitted coaxially with a snap-fit or snap-lock action onto the syringe barrel. Importantly, this sliding and press-fit placement of the guard sleeve 24 onto the syringe barrel 18 may be performed quickly and easily by one person, e.g., with the syringe 12 supported on a flat and stable surface. The guard sleeve can be safely manipulated and fitted onto the syringe barrel, by controllably press-fitting the sleeve onto a rear portion of the syringe barrel with a forward sliding motion.

Figure 5:
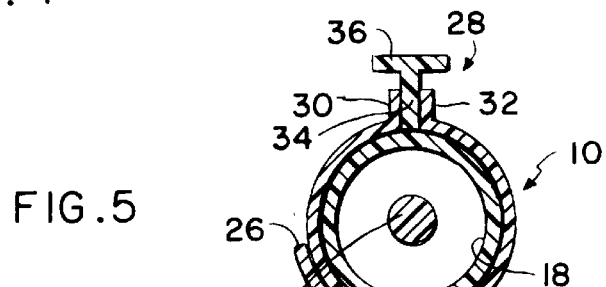
FIG. 5 is an enlarged transverse sectional view taken generally on the line 5—5 of FIG. 4.
Figure 6:
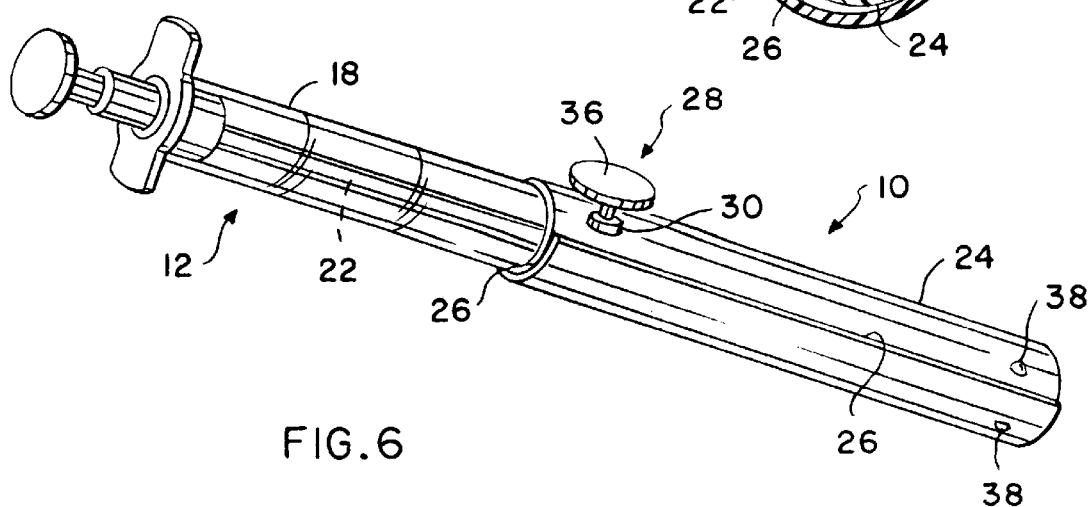
FIG. 6 is a perspective view showing the needle guard in the fully installed position of FIG. 5.

On the syringe barrel 18, the guard sleeve 24 expands sufficiently in diametric size to fit relatively snugly thereon (FIG. 5). The guard sleeve 24 can then be slidably advanced on the syringe barrel so that the front end of the guard sleeve protrudes therefrom in surrounding and protective relation to the hypodermic needle 14. Such slidable positioning of the guard sleeve preferably takes place while holding the syringe 12 with the needle 14 pointed away from the person. The guard sleeve 24 is positioned on the barrel 18 so that the front end of the guard sleeve 24 protrudes at least a short distance beyond the sharp tip end of the needle 14, as viewed in FIGS. 4 and 6, to protect against inadvertent or accidental contact with the needle 14. Importantly, the guard sleeve 24 has sufficient longitudinal stiffness to prevent significant deformation or collapse when bumped or dropped, thereby providing a sufficiently rigid structure to prevent undesired human contact with the sharp tip end of the needle 14.

The needle guard 10 additionally includes a lock member such as a thumbscrew 28 for releasibly locking the guard sleeve 24 onto the syringe barrel 18. More specifically, as shown, an internally threaded boss 30 is mounted on or formed integrally with the guard sleeve 24 at a selected location preferably at or near the rear or proximal end thereof. The threaded boss 30 defines a radially open threaded port 32 (FIG. 5) for receiving a threaded stem 34 of the thumbscrew 28. As shown, a radially inboard end of this threaded stem 34 can thus be advanced within the boss 30 for secure gripping engagement with the underlying external surface of the syringe barrel 18, when the needle guard is mounted thereon. A radially outboard end of the threaded stem 34 is coupled to a comparatively large diameter thumb wheel 36 adapted for fingertip rotation to advance or retract the stem 34 within the boss 30, as desired. In a preferred form, the thumbscrew 28 is formed from a hard material such as metal or the like, and the distal end of the stem 34 is pointed for secure and biting engagement with the typically plastic material of the syringe barrel 18.

Accordingly, the needle guard 10 can be fitted quickly and easily and safely over the syringe barrel 18 in a position surrounding and protecting against access to the sharp hypodermic needle 14, followed by rotation of the thumb wheel 36 to lock the threaded stem 34 tightly against the barrel exterior. In this position, the relatively stiff guard sleeve 24 projects from the barrel nose end 16 a sufficient distance beyond the pointed tip of the needle 14 to minimize and substantially prevent undesired and/or accidental personnel contact with the sharp needle tip. In this regard, the guard sleeve 24 is adapted to fit quickly and easily onto syringes having a range of diametric barrel sizes, with the longitudinal marginal edges 26 of the guard sleeve 24 desirably remaining in an least slightly scrolled or overlapping relation (as viewed in FIG. 5) when mounted onto the syringe barrel. The guard sleeve 24 has sufficient structural stiffness and tensile strength to protect against needle access or contact, despite potentially rough handling or dropping of the syringe. For substantially optimized locking force between the thumbscrew 28 and the syringe barrel 18, the threaded boss 30 is desirably spaced circumferentially from the inner one of the overlapped marginal edges 26 by an arcuate span significantly less than 180°, and preferably about 30° to 120° as depicted in FIG. 5. While FIG. 5 shows the thumbscrew 28 spaced closer to the underlapping marginal edge, it will be recognized and understood that the thumbscrew can be positioned closer to the overlapping marginal edge, if desired. Upon removal from the syringe barrel 18, the guard sleeve 24 springably returns to the initial partially collapsed and reduced diameter configuration (FIG. 1) and can be re-used.

Figure 7:
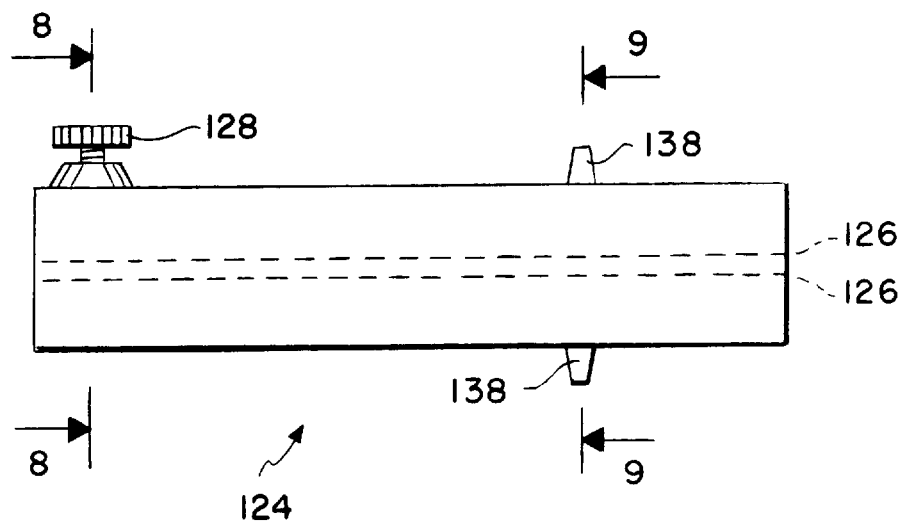
FIG. 7 is a top plan view showing an alternative preferred embodiment of the syringe needle guard of the present invention.
Figure 8:
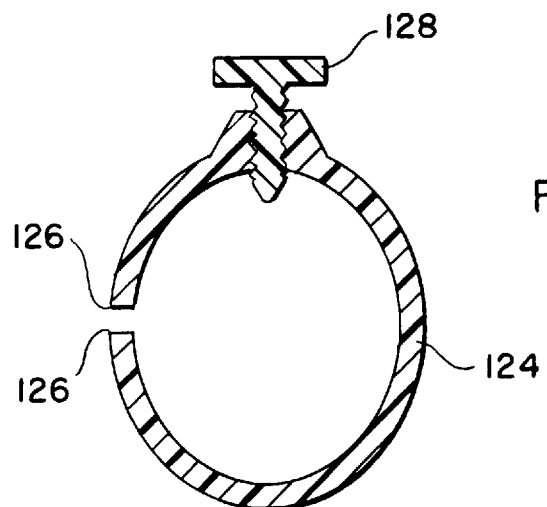
FIG. 8 is an enlarged transverse sectional view taken generally on the line 8—8 of FIG. 7.
Figure 9:
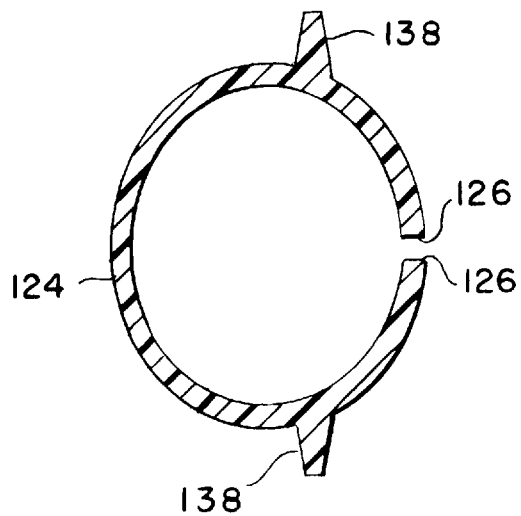
FIG. 9 is an enlarged transverse sectional view taken generally on the line 9—9 of FIG. 7.

FIGS. 7–9 illustrate an alternative preferred embodiment of the invention, wherein a modified guard sleeve 124 has a generally tubular and longitudinally split construction to define longitudinal marginal edges 126 in closely adjacent but non-overlapping or unscrolled relation. This modified guard sleeve 124 may be constructed from a lightweight yet relatively stiff sheet of plastic material which is rolled and set to this longitudinally split sleeve configuration, or alternately the guard sleeve 124 may be formed by other processes such as extrusion or by injection molding. The resultant guard sleeve 124 has sufficient radial resilience to permit the marginal edges 126 at a front end thereof to be separated sufficiently for substantially snap-fit or snap-lock mounting onto a syringe barrel, in the same manner as previously described with respect to the embodiment of FIGS. 1–6. Such separation of the marginal edges 126 at the sleeve front end may occur by manipulation of radially outwardly protruding tabs 138 formed on the guard sleeve 124 at or near the front end thereof. Alternately such separation may occur as an incident to pressing the marginal edges 126 against the syringe barrel without requiring prior manual separation. FIG. 9 illustrates the tabs 138 positioned at generally symmetric locations each spaced circumferentially on opposite sides of the split marginal edges 126 by an arcuate span of less than 90°. FIG. 8 shows a thumbscrew 128 mounted at or near a rear end of the guard sleeve 124 for releasably locking the sleeve onto a syringe barrel in the same manner as previously described.

A variety of further modifications and improvements in and to the improved syringe needle guard of the present invention will be apparent to those skilled in the art. Accordingly, no limitation on the invention is intended by way of the foregoing description and accompanying drawings, except as set forth in the appended claims.

What is claimed is:

1. A needle guard for mounting onto a syringe barrel to safeguard against inadvertent contact with a hypodermic needle protruding from a nose end of the syringe barrel, said needle guard comprising:

an elongated guard sleeve having a longitudinally split construction to define a pair of longitudinally extending marginal edges, said guard sleeve being formed from a relatively stiff material having sufficient resilience to permit separation of said marginal edges to accommodate substantially snap-fit mounting onto a syringe barrel in a position with a front end of said guard sleeve protruding at least slightly beyond a pointed tip end of a hypodermic needle protruding from the syringe barrel; and further including means for manual separation of said marginal edges of said guard sleeve sufficiently for accommodating substantially snap-fit mounting of said guard sleeve onto the syringe barrel.

2. The needle guard of claim 1 wherein said guard sleeve is formed from a lightweight plastic material.

3. The needle guard of claim 1 wherein said longitudinally extending marginal edges of said guard sleeve are formed in overlapping relation.

4. The needle guard of claim 1 wherein said longitudinally extending marginal edges of said guard sleeve are formed in closely spaced relation.

5. The needle guard of claim 1 wherein said separation means comprises a pair of radially outwardly projecting tabs formed on said guard sleeve at a position generally adjacent said front end thereof.

6. The needle guard of claim 1 further including means for releasibly locking said guard sleeve onto a syringe barrel.

7. The needle guard of claim 6 wherein said locking means comprises a thumbscrew carried by said guard sleeve.

8. The needle guard of claim 7 wherein said thumbscrew is carried by said guard sleeve at a position generally adjacent a rear end thereof.

9. The needle guard of claim 8 wherein said thumbscrew has a pointed tip for biting engagement with a syringe barrel.

10. A needle guard for mounting onto a syringe barrel to safeguard against inadvertent contact with a hypodermic needle protruding from a nose end of the syringe barrel, said needle guard comprising:

an elongated guard sleeve having a longitudinally split construction to define a pair of longitudinally extending marginal edges, said guard sleeve being formed from a relatively stiff material having sufficient resilience to permit separation of said marginal edges to accommodate substantially snap-fit mounting onto a syringe barrel in a position with a front end of said guard sleeve protruding at least slightly beyond a pointed tip end of a hypodermic needle protruding from the syringe barrel;

means for manual separation of said marginal edges at the front end of said guard sleeve sufficiently for accommodating substantially snap-fit mounting of said guard sleeve onto a syringe barrel; and means for releasibly locking said guard sleeve onto a syringe barrel.

11. The needle guard of claim 10 wherein said guard sleeve is formed from a lightweight plastic material.

12. The needle guard of claim 11 wherein said longitudinally extending marginal edges of said guard sleeve are formed in overlapping relation.

13. The needle guard of claim 11 wherein said longitudinally extending marginal edges of said guard sleeve are formed in closely spaced relation.

14. The needle guard of claim 11 wherein said separation means comprises a pair of radially outwardly projecting tabs formed on said guard sleeve at a position generally adjacent said front end thereof.

15. The needle guard of claim 11 wherein said locking means comprises a thumbscrew carried by said guard sleeve.

16. The needle guard of claim 15 wherein said thumbscrew is carried by said guard sleeve at a position generally adjacent a rear end thereof.

17. A needle guard for mounting onto a syringe barrel to safeguard against inadvertent contact with a hypodermic needle protruding from a nose end of the syringe barrel, said needle guard comprising:

an elongated guard sleeve having a longitudinally split construction to define a pair of longitudinally extending marginal edges, said guard sleeve being formed from a relatively stiff material having sufficient resilience to permit separation of said marginal edges to accommodate substantially snap-fit mounting onto a syringe barrel in a position with a front end of said guard sleeve protruding at least slightly beyond a pointed tip end of a hypodermic needle protruding from the syringe barrel; and further including means for releasibly locking said guard sleeve onto a syringe barrel.

18. The needle guard of claim 17 wherein said guard sleeve is formed from a lightweight plastic material.

19. The needle guard of claim 18 wherein said longitudinally extending marginal edges of said guard sleeve are formed in overlapping relation.

20. The needle guard of claim 18 wherein said longitudinally extending marginal edges of said guard sleeve are formed in closely spaced relation.

* * * * *